United States Patent
McBroom et al.

(10) Patent No.: US 6,277,108 B1
(45) Date of Patent: Aug. 21, 2001

(54) INTRODUCER WITH LOCATION MARKER

(75) Inventors: Jeffrey A. McBroom, Champlin; David A. Liebl, Eden Prairie, both of MN (US)

(73) Assignee: MedAmicus, Inc., Minneapolis, MN (US)

( * ) Notice: Subject to any disclaimer, the term of this patent is extended or adjusted under 35 U.S.C. 154(b) by 0 days.

(21) Appl. No.: 09/326,901

(22) Filed: Jun. 4, 1999

(51) Int. Cl.⁷ .............................................. A61M 25/098
(52) U.S. Cl. .......................................................... 604/529
(58) Field of Search ........................... 606/108; 604/161, 604/160, 167, 529, 103.1

(56) References Cited

U.S. PATENT DOCUMENTS

| | | | |
|---|---|---|---|
| 3,605,750 | * 9/1971 | Sheridan et al. | 604/529 |
| 4,571,240 | * 2/1986 | Samson et al. | 604/96 |
| 4,796,637 | 1/1989 | Masuch et al. | 128/658 |
| 4,938,220 | * 7/1990 | Mueller, Jr. | 128/658 |
| 5,045,071 | 9/1991 | McCormick et al. | 604/280 |
| 5,076,278 | 12/1991 | Vilkomerson et al. | 128/662.03 |
| 5,129,883 | 7/1992 | Black | 604/101 |
| 5,161,536 | 11/1992 | Vilkomerson et al. | 128/660.07 |
| 5,174,302 | 12/1992 | Palmer | 128/772 |
| 5,209,730 | 5/1993 | Sullivan | 604/96 |
| 5,259,837 | 11/1993 | Van Wormer | 604/96 |
| 5,320,602 | * 6/1994 | Karpiel | 604/54 |
| 5,334,143 | 8/1994 | Carroll | 604/54 |
| 5,345,938 | 9/1994 | Nishiki et al. | 128/660.04 |
| 5,385,563 | 1/1995 | Gross | 604/284 |
| 5,406,959 | 4/1995 | Mann | 128/753 |
| 5,419,324 | 5/1995 | Dillow | 128/653.1 |
| 5,423,755 | 6/1995 | Kesten et al. | 604/96 |
| 5,427,115 | 6/1995 | Rowland et al. | 128/756 |
| 5,429,617 | 7/1995 | Hammersmark et al. | 604/264 |
| 5,439,445 | 8/1995 | Kontos | 604/96 |
| 5,485,840 | 1/1996 | Bauman | 128/660.03 |
| 5,535,756 | 7/1996 | Parasher | 128/756 |
| 5,558,652 | 9/1996 | Henke | 604/280 |
| 5,690,666 | * 11/1997 | Berenstein et al. | 606/191 |
| 5,948,489 | * 9/1999 | Hopkins | 604/529 |

* cited by examiner

Primary Examiner—Sharon Kennedy
(74) Attorney, Agent, or Firm—Schwegman, Lundberg, Woessner & Kluth, P.A.

(57) ABSTRACT

An introducer system has a splittable sheath which includes a marker band. The marker band allows the sheath to be viewed under fluoroscopy while inserted within a patient, and while still allowing a medical device to be introduced therethrough. In addition, the marker band allows for the sheath to be split using a slitter in a longitudinal direction which permits the sheath to be removed from the venous system without having to be withdrawn over an end of the medical device. The marker band has perforations, comprises a mesh structure, or can comprise a braid structure, which each allow for the sheath, and the marker band, to be slittable.

22 Claims, 3 Drawing Sheets

US 6,277,108 B1

INTRODUCER WITH LOCATION MARKER

FIELD OF THE INVENTION

The present invention relates generally to a splittable introducer for insertion of a catheter, guide wire and other medical devices into a patient. More particularly, it pertains to a splittable introducer employed for indicating a position of a device located within a body.

BACKGROUND OF THE INVENTION

Introducer devices are employed for inserting catheters, guide wires, or other medical devices into patients. A typical procedure provides for insertion of a needle into the vasculature of a patient. After insertion of the needle, a guide wire is inserted through the needle, and the needle is removed. The dilator and the sheath are inserted over the guidewire, and the dilator may be removed leaving the sheath protruding from the patient's vein. A diagnostic or therapeutic catheter (e.g. a central venous access catheter) or guide wire or other medical device, is then inserted through the sheath into the patient.

The catheter or medical device which is inserted through the introducer, depending on the application, must be positioned precisely within the vasculature or tissue of the patient. However, once inserted, it is difficult to monitor the location of the introducer and/or the medical device inserted into the patient.

In addition, the catheter is coupled with other medical devices before the introducer is removed. It is therefore necessary to carefully remove the introducer without disturbing the catheter. To remove the introducer, the encasing sheath is then typically longitudinally sheared and removed from the catheter or guide wire and the patient such as by applying opposing force to opposed wings or tabs of the introducer device.

Accordingly, what is needed is an introducer, the location of which can be identified while inserted into a vasculature of a patient. What is further needed is an introducer which can be easily removed once inserted into a patient.

SUMMARY OF THE INVENTION

An introducer for use with a medical device is described where the introducer includes a severable elongate sheath adapted to be inserted into a circulatory system to a desired location in a vessel. The elongate sheath is severable such that it can be removed from medical devices inserted therethrough without disturbing or removing the medical device from the patient. The sheath extends from a proximal end to a distal end and includes an elongate passage. In addition, a radiopaque marker band is coupled with the severable sheath and, in one embodiment, is disposed proximate to the distal end of the elongate sheath, where the marker band is severable. In one embodiment, the distal end of the severable sheath is thermoformed around the severable marker band.

The severable marker band is formed, in one embodiment, from a thin structure of material in order to facilitate its severability. In one embodiment, the severable marker band has a thickness of 0.0015 inches. In another embodiment, the severable marker band has a thickness of 0.0025 inches. Alternatively, the severable marker band has a thickness between about 0.0005–0.005 inches.

In another embodiment, the severable marker band includes at least one aperture therein, or alternatively, the severable marker band includes a plurality of apertures therein. Alternatively, the severable marker band includes a perforated line to permit severability of the marker band. The severable marker band can extend between side edges of the marker band, or can be disposed between a top edge and a bottom edge of the marker band. In yet another embodiment, the severable marker band is formed of a braided material. Alternatively, the marker band is formed of a porous material, such as a mesh screen. The marker band is alternatively severable by forming a slot in the marker band.

In another embodiment, a system for use in fluoroscopy is provided. An introducer for use with a medical device includes a severable elongate sheath adapted to be inserted into a circulatory system to a desired location in a vessel. The elongate sheath is severable such that it can be removed from medical devices inserted therethrough without disturbing or removing the medical device from the patient. The sheath extends from a proximal end to a distal end and includes an elongate passage. In addition, a radiopaque marker band is coupled with the severable sheath and, in one embodiment, is disposed proximate to the distal end of the elongate sheath, where the marker band is severable. In addition, a means for severing the introducer is provided, which can include a slitter, a rip-cord, a weakened portion, or other means.

Advantageously, the introducer with marker band allows for improved visibility of the introducer under fluoroscopy, and permits a practitioner to identify the location of the introducer relative to the location of the intended implant device. The various configurations of the marker band allow for the introducer and the marker band to be splittable. In addition, the marker band remains securely attached to the introducer to prevent dislodgement therefrom during slitting of the introducer.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
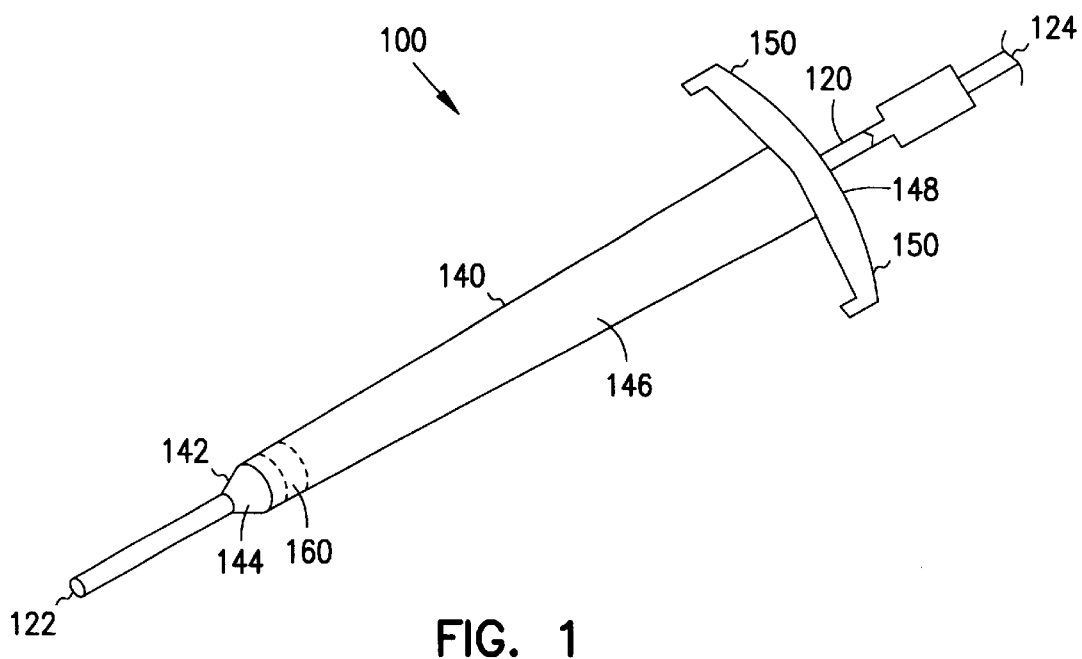
FIG. 1 is a perspective view illustrating a splittable introducer constructed in accordance with one embodiment of the present invention.

FIG. 1 illustrates a splittable assembly 100 for use with the present invention. The splittable assembly 100 includes generally a sheath 140 and an optional dilator 120. The dilator 120 allows for the splittable assembly 100 to be introduced into a vein of a patient, for instance, over a guidewire. The dilator 120 extends from a distal end 122 to a proximal end 124, where the distal end 122 is insertable into a patient. The dilator 120 also includes a passage therethrough to allow the dilator to be inserted over a guidewire or a catheter. The dilator 120 is sized to be received by the sheath 140 therein.

The sheath 140 allows for additional instruments to be inserted therethrough and inserted into the patient. The sheath 140 includes various types of sheaths, for instance, the sheath 140 can comprise a sheath which has a strengthening braid of material. Alternatively, the sheath 140 includes those which are modified to prevent bends in the elongate sheath. The sheath 140 extends from a distal end 142 to a proximal end 148, where the distal end 142 is first inserted into the patient and the proximal end 148 remains outside of the patient. Near the distal end 142 is a tapered portion 144 which provides a transition to a cylindrical portion 146. Near the proximal end 148 of the sheath 140 are tabs 150 which allow for the sheath 140 to be manipulated. The sheath 140 also includes a passage therethrough which allows for the introduction of the dilator 120 therein. Once the dilator 120 is removed, other medical instruments can be easily inserted into and through the sheath 140, and introduced into a patient.

The sheath 140 is splittable such that the sheath 140 is separable into two or more components. The sheath 140 is separable or splittable which prevents disruption to or removal of instruments or devices which have been inserted through the sheath 140. The splittable sheath 140 is splittable in a number of manners such as by using a slitter, as further described below. Alternatively, the sheath 140 is splittable using a rip cord or strengthening strip running along the longitudinal length of the sheath, a weakening which allows the introducer to be ripper apart, or other techniques which are also to those skilled in the art.

The sheath 140 further includes a marker band 160 coupled therewith. In one embodiment, the marker band 160 is coupled with the sheath 140 proximate to the distal end 142 of the sheath 140. The marker band 160 allows a practitioner to visualize the sheath 140 when it is inserted into a patient, as will be further described below. It should be noted that a plurality of marker bands can also be provided. The marker band 160 and the sheath 140 are both severable. In one embodiment, the marker band 160 forms a ring of material. Alternatively, in another configuration, the marker band 160 includes other configurations such as a partial ring of material, or a band formed in another shape. In addition, the marker band 160 is coupled with the sheath 140 such that as the sheath 140 is severed, the marker band 160 is also severed. The marker band 160 is coupled with the sheath such that the marker band 160 remains secured to the sheath 140 when the sheath 140 is severed.

Figure 2:
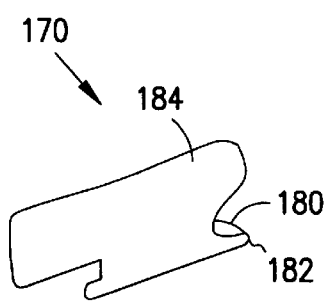
FIG. 2 is a perspective view illustrating a slitter constructed in accordance with the one embodiment of the present invention.

FIG. 2 illustrates a slitter 170 for use with the splittable assembly 100 shown in FIG. 1. The slitter 170 includes a cutting blade 180 which is used to separate the sheath 140 into multiple components, allowing easy removal from a patient. The slitter 170 also includes a handle 184 with which a user manipulates the slitter 170 relative to the sheath 140. The slitter 170 is manipulated to separate the sheath 140 into multiple components. As mentioned above, there are many ways to separate the sheath 140, and the slitter 170 is one example.

Figure 3:
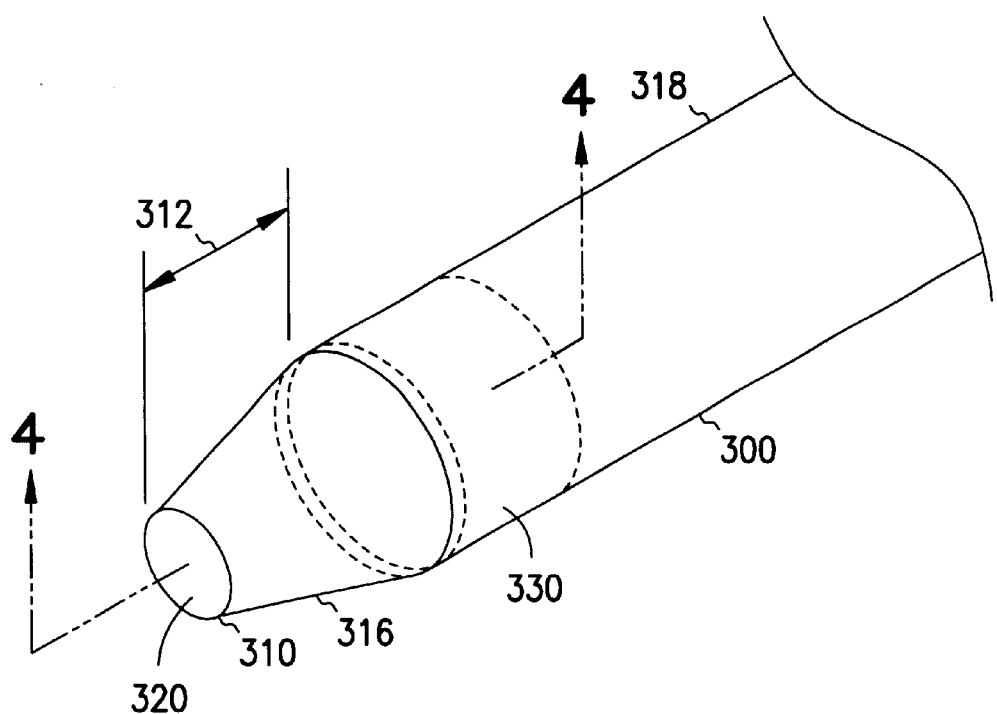
FIG. 3 is a perspective view illustrating a portion of a splittable introducer constructed in accordance with one embodiment of the present invention.

As discussed above, the splittable assembly 100 includes a splittable sheath 140 which has a marker band coupled therewith. FIG. 3 illustrates the sheath 300 in greater detail. The distal tip 310 includes a tapered portion 316 which transitions to a cylindrical portion 318 along 312. Coupled within the cylindrical portion 318 is a marker band 330. The marker band 330 does not interfere with the bore 320 of the sheath 300, such that instruments can be inserted therethrough. For instance, the marker band 330 comprises a ring of material which has its radial axis aligned with the radial axis of the sheath 140. The marker band 330 is adapted to be splittable or slittable, as will be further described below. In addition, the marker band 330 is adapted to be visible under fluoroscopy. The marker band 330 allows for a practitioner to identify, in one embodiment, the location of the distal tip 310 of the sheath 300 while it is inserted into a patient. To facilitate the visibility of the marker band 330, the marker band 330 is comprised of a radiopaque material. In addition, the marker band 330 should also be comprised of a biocompatible material. Examples of materials which would be appropriate, although not limited to, include a metal such as gold, platinum, silver, or any polymer with high concentrations of radiopaque material.

Figure 4:
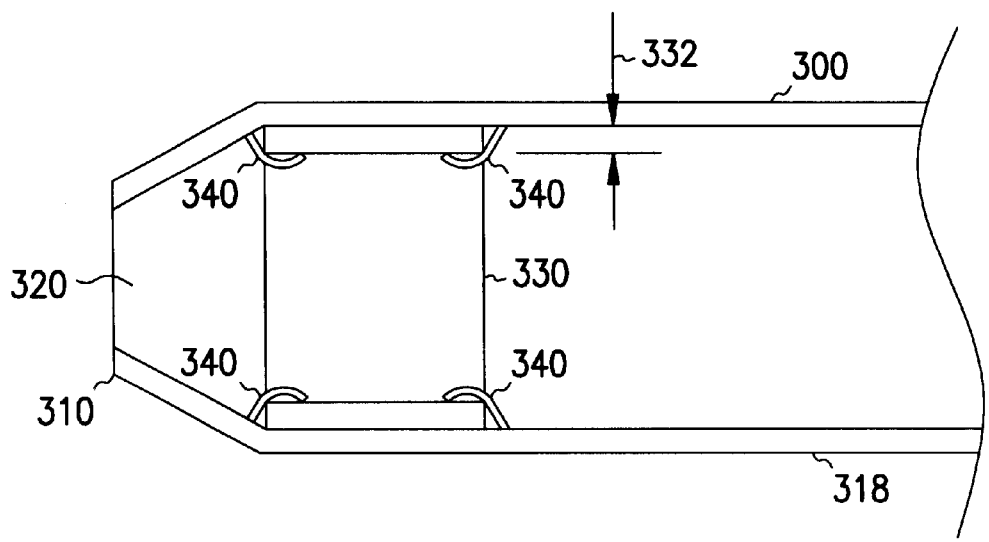
FIG. 4 is a cross-section view illustrating a portion of a splittable introducer constructed in accordance with another embodiment of the present invention.

FIG. 4 illustrates a first embodiment of a marker band 330. It should be noted that the marker band is splittable, and the various embodiments described below can be combined to form alternative configurations of the present invention. In one embodiment, the marker band 330 comprises a thin marker band which allows for the marker band to be slittable. In one embodiment, the marker band 330 has a thickness 332 of 0.0015 inches. In another embodiment, the marker band 330 has a thickness 332 of 0.0025 inches. In yet another embodiment, the marker band 330 has a thickness 332 which ranges from 0.0005 inches to 0.005 inches.

The marker band 330 is held securely in place to the sheath 300, so as to prevent dislodging during slitting of the sheath 300. The marker band 330 can be fixed to the sheath 300 in a number of manners. In one embodiment, the marker band 330 is encapsulated during thermoforming of the sheath 300, as is shown in FIG. 4. Alternatively, the marker band 330 can be secured to the sheath 300 in other manners, such as adhesive. Material 340 which forms part of the sheath 300, is disposed over a portion of the marker band 330. The material 340 does not interfere with the radiopaque visibility of the marker band 330.

Figure 5:
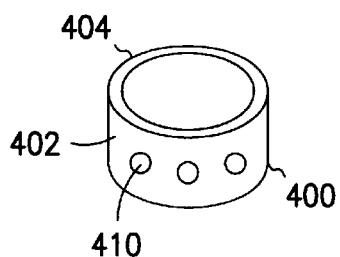
FIG. 5 is a perspective view illustrating a marker band constructed in accordance with one embodiment of the present invention.

FIGS. 5–9 illustrate other embodiments of a marker band which is slittable, and yet adheres well to the sheath 300. FIG. 5 illustrates a marker band 400 which includes an external surface 402 and an internal surface 404. The marker band 400 includes at least one aperture 410 therein. In one embodiment, the aperture 410 is sized such that material of the sheath 300 is disposed in the aperture 410 during the thermoforming process. In another embodiment, the marker band 400 includes a plurality of apertures which allow for the marker band 400 to be splittable. In another embodiment, the aperture 410 extends from the internal surface 404 to the external surface 402. Alternatively, the aperture 410 can be only partially disposed therethrough.

Figure 6:
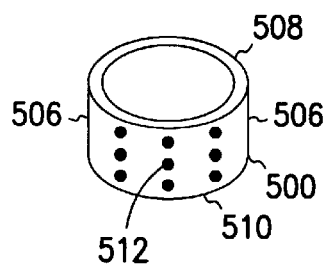
FIG. 6 is a perspective view illustrating a marker band constructed in accordance with another embodiment of the present invention.
Figure 7:
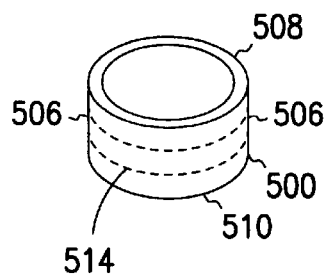
FIG. 7 is a perspective view illustrating a marker band constructed in accordance with yet another embodiment of the present invention.

FIG. 6 illustrates yet another embodiment of a marker band 500. The marker band 500 extends from a top surface 508 to a bottom surface 510 and has side edges 506. The marker band 500, in one embodiment, includes vertical perforations 512 which extend from the top surface 508 to the bottom surface 510. In another embodiment, additional rows of the vertical perforations 512 can be included which extend from the top surface 508 to the bottom surface 510. In yet another embodiment, the marker band 500 includes horizontal perforations 514 which extend between the side edges 506, as shown in FIG. 7. Types of perforations used for these embodiments can vary. For instance, the perforations can include a series of slits within the marker band 500. Alternatively, the perforations can include a plurality of weakened surfaces, with or without the slits, and/or a weakened line in the material to allow the marker band 500 to be splittable. In addition, the perforations allow for a mechanical bond to occur between the marker band and the sheath tubing wall when the sheath is thermoformed.

Figure 8:
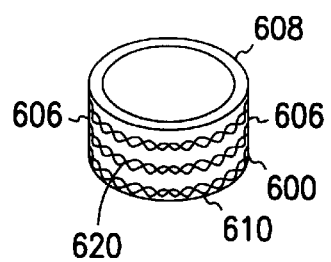
FIG. 8 is a perspective view illustrating a marker band constructed in accordance with another embodiment of the present invention.

FIG. 8 illustrates yet another embodiment of the present invention. A marker band 600 is provided which extends from a top surface 608 to a bottom surface 610, and has side edges 606. The marker band 600 is comprised of braided material 620, as shown in the figure. The braid allows for an increased surface area which allows for better bonding between the sheath and the marker band 600 during molding of the sheath. In addition, the reduced mass of the braided material 620 allows for the amount of slitting force to be reduced, thereby facilitating the slittable nature of both the sheath and the marker band 600.

Figure 9:
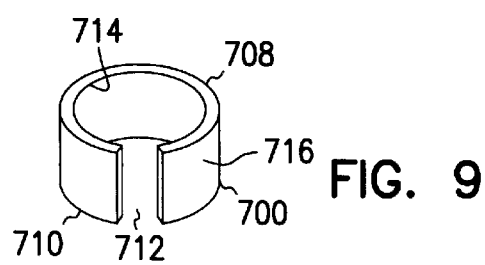
FIG. 9 is a perspective view illustrating a marker band constructed in accordance with one embodiment of the present invention.

FIG. 9 illustrates another embodiment of a marker band 700, which extends from a top surface 708 to a bottom surface 710. In one embodiment, the marker band 700 includes a vertical slot 712, as shown in the figure. The slot 712 extends from the top surface 708 to the bottom surface 710, or alternatively, extends only partially in between the top surface 708 and the bottom surface 710, which allows for the marker band 700 to be slittable. In another embodiment, the slot 712 extends through the marker band 700 from an external surface 716 to an internal surface 714 of the marker band 700. Alternatively, the slot 712 extends only partially in between the internal surface 714 and the external surface 716. The slot 712 of the marker band 700 allows for the marker band 700 to be slittable as it is disposed within the sheath.

Figure 10:
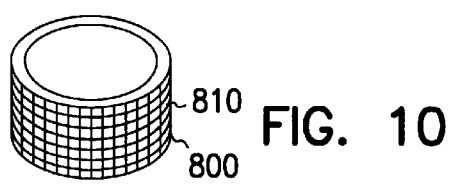
FIG. 10 is a perspective view illustrating a marker band constructed in accordance with another embodiment of the present invention.

FIG. 10 illustrates yet another embodiment of a marker band 800. The marker band 800 has a similar shape as those embodiments discussed above, however, the marker band 800 is comprised of a mesh screen 810. The mesh screen allows for the marker band 800 to be slittable. Alternatively, the marker band 800 could also be comprised of a porous material which allows for the marker band to be slittable.

The introducer with the slittable marker band allows for improved visibility of the introducer under fluoroscopy, and permits a practitioner to identify the location of the introducer relative to the location of the intended implant device. The various configurations of the marker band allow for the introducer and the marker band to be splittable, and easily removed from a medical device inserted into a patient. In addition, the marker band remains securely attached to the introducer to prevent dislodgement therefrom during slitting of the introducer.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. An introducer for use with a medical device, the introducer comprising:

a severable elongate sheath adapted to be inserted into a circulatory system, the sheath extending from a proximal end to a distal end and including an elongate passage therethrough; and a radiopaque marker band comprising coupled with a portion of the severable sheath, the metal marker band being severable as the elongate sheath is severed, the severable marker band including at least one perforated line.

2. The introducer as recited in claim 1, wherein the severable marker band is disposed proximate to the distal end of the elongate sheath.

3. The introducer as recited in claim 1, wherein the distal end of the severable sheath is thermoformed around the severable marker band.

4. The introducer as recited in claim 1, wherein the severable marker band has a thickness of 0.0015 inches.

5. The introducer as recited in claim 1, wherein the severable marker band has a thickness of 0.0025 inches.

6. The introducer as recited in claim 1, wherein the severable marker band has a thickness between about 0.0005–0.005 inches.

7. The introducer as recited in claim 1, wherein the severable marker band includes at least one aperture there in.

8. The introducer as recited in claim 7, wherein the severable marker band includes a plurality of apertures therein.

9. The introducer as recited in claim 1, wherein the at least one perforated line extends between side edges of the severable marker band.

10. The introducer as recited in claim 1, wherein the at least one perforated line extends between a top edge and a bottom edge of the severable marker band.

11. The introducer as recited in claim 1, wherein the severable marker band is formed of a braided material.

12. The introducer as recited in claim 1, wherein the severable marker band is formed of a porous material.

13. The introducer as recited in claim 12, wherein the porous material comprises a mesh screen.

14. The introducer as recited in claim 1, wherein the severable marker band includes a slot extending from a top surface of the severable marker band to a bottom surface of the severable marker band.

15. An apparatus for use in fluoroscopy comprising:

an introducer including:
- a severable elongate sheath adapted to be inserted into a circulatory system, the sheath extending from a proximal end to a distal end and including an elongate passage therethrough;
- radiopaque metal marker band comprising a metal coupled with a portion of the severable sheath, the marker band being severable as the elongate sheath is severed, the severable marker band including at least one perforated line; and a means for severing the elongate sheath.

16. The apparatus as recited in claim 15, wherein the severable marker band is disposed proximate to the distal end of the elongate sheath.

17. The apparatus as recited in claim 15, wherein the means for severing the elongate sheath comprises a slitter.

18. The apparatus as recited in claim 15, wherein the severable marker band is formed of gold or platinum.

19. The apparatus as recited in claim 15, wherein the severable marker band is formed of silver.

20. A system for use in fluoroscopy comprising:

an introducer including:
- a severable elongate sheath adapted to be inserted into a circulatory system, the sheath extending from a proximal end to a distal end and including an elongate passage therethrough; and
- radiopaque metal marker band comprising a metal coupled with the severable sheath and disposed proximate to the distal end of the elongate sheath, the marker band being severable as the elongate sheath is severed, the severable marker band including at least one perforated line; and a dilator receivable by the elongate passage of the introducer.

21. The system as recited in claim 20, further comprising a slitter adapted for severing the elongate sheath.

22. The system as recited in claim 20, wherein the severable marker band is formed of a porous material.

* * * * *

UNITED STATES PATENT AND TRADEMARK OFFICE
CERTIFICATE OF CORRECTION

PATENT NO. : 6,277,108 B1
DATED : August 21, 2001
INVENTOR(S) : Jeffery A. McBroom and David A. Liebl It is certified that error appears in the above-identified patent and that said Letters Patent is hereby corrected as shown below:

Column 6,
Line 48, delete "there in" and insert -- therein --, therefor.

Column 7,
Line 7, insert -- a -- between "therethrough;" and "radiopaque".; and delete "metal" afer "radiopaque".

Column 8,
Line 7, insert -- a -- between "and" and "radiopaque".; and delete "metal" after "radiopaque".

Signed and Sealed this

Sixteenth Day of July, 2002

Attest:

JAMES E. ROGAN
Attesting Officer  Director of the United States Patent and Trademark Office